United States Patent
Malmberg et al.

(10) Patent No.: US 6,794,164 B2
(45) Date of Patent: Sep. 21, 2004

(54) PROCESS FOR THE ISOLATION OF POLYHYDROXY CYCLIC CARBOXYLIC ACIDS

(75) Inventors: Mats Malmberg, Lund (SE); Brita Westrup, Lund (SE)

(73) Assignee: Novozymes Biopharma AB, Lund (SE)

( * ) Notice: Subject to any disclaimer, the term of this patent is extended or adjusted under 35 U.S.C. 154(b) by 23 days.

(21) Appl. No.: 10/041,865

(22) Filed: Jan. 7, 2002

(65) Prior Publication Data

US 2003/0138920 A1 Jul. 24, 2003

(51) Int. Cl.$^7$ .......................... C12P 7/40; C07C 313/00; C07C 229/42; A61K 38/43
(52) U.S. Cl. ...................... 435/136; 562/125; 562/128; 562/507; 562/510; 424/94.1
(58) Field of Search .................. 435/136; 502/125, 502/128, 507, 510; 424/94.1

(56) References Cited

U.S. PATENT DOCUMENTS

| | | | |
|---|---|---|---|
| 3,546,372 A | 12/1970 | Araki et al. | 195/47 |
| 4,769,061 A | 9/1988 | Comai | 504/206 |
| 5,214,165 A | 5/1993 | Sutherland et al. | 549/433 |
| 5,605,818 A | 2/1997 | Katsumata et al. | 435/108 |
| 6,472,169 B1 * | 10/2002 | Frost et al. | 435/41 |
| 6,613,552 B1 * | 9/2003 | Frost et al. | 435/136 |

OTHER PUBLICATIONS

"Recovery of Shikimic Acid Using Temperature–Swing Complexation Extraction and Displacement Back Extraction," Miles, et al., *Isolation & Purification*, 1994, vol. 2, pp 75–82.

"The Biosynthesis and Synthesis of Shikimic Acid, Chorismic Acid and Related Compounds," Campbell, et al., *Synthesis*, Feb., 1993, pp. 179–193.

"Chemical Synthesis of Shikimic Acid and Its Analogues," Jiang, et al., *Tetraedron* Report No. 449, vol. 54, 1998, pp 4697–4753.

* cited by examiner

Primary Examiner—Herbert J. Lilling
(74) Attorney, Agent, or Firm—Standley Law Group LLP

(57) ABSTRACT

This invention is directed to the use of crystallization acids, such as acetic, lactic and propionic acids, to obtain high purity polyhydroxyl cyclic carboxylic acids (PCCA) from low purity aqueous solutions. The preferred PCCA is shikimic acid and the preferred crystallization acid is acetic acid. The method according to the invention is particularly applicable to the isolation of shikimic acid from a fermentation broth.

16 Claims, No Drawings

US 6,794,164 B2

PROCESS FOR THE ISOLATION OF POLYHYDROXY CYCLIC CARBOXYLIC ACIDS

TECHNICAL FIELD

This invention relates to a method for the isolation of high purity polyhydroxy cyclic carboxylic acids (PCCA), such as shikimic acid, from aqueous solutions. More particularly, this invention relates to the isolation of shikimic acid from a fermentation broth through the use of an organic acid such as acetic acid.

BACKGROUND OF THE INVENTION

This invention relates to PCCAs and to derivatives of PCCAs that are isolated in high purity from aqueous solutions, such as fermentation broths produced by microorganisms. As used herein, PCCAs are a group of primarily organic molecules that possess two or more hydroxyl groups, a non-aromatic ring structure, at least one carbonyl group and a water solubility of at least 10 gms per 100 ml at room temperature. Representative PCCAs include shikimic acid, quinic acid, 5-dehydroshikimic acid, 6-fluoroshikimic acid and derivatives thereof. A preferred PCCA in the process of the present invention is shikimic acid. Shikimic acid is an intermediate metabolite in the common or shikimate pathway of plants and microorganisms. PCCAs are useful as starting materials for antibacterial, antifungal and herbicidal agents and as nutritionals. The invention in general is directed to novel processes for the preparation and isolation of these compounds.

The shikimic acid pathway is essential for the existence of bacteria and plants as it provides for the synthesis of necessary metabolites. In bacteria, the pathway provides not only the three (3) aromatic α-amino acids (tyrosine, tryptophan and phenylalanine) but also paraaminobenzoic acid, parahydroxybenzoic acid, salicyclic acid and the like. The shikimic acid pathway is well known and well reported in the literature.

Shikimic acid (3,4,5-trihydroxy-1-cyclohexene-1-carboxylic acid) has three (3) chiral centers, which make six (6) different optical isomers possible. A preferred product produced according to the present invention is the natural levorotatory L-shikimic acid of the structural formula:

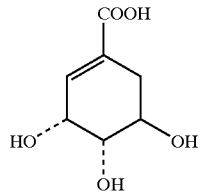

One embodiment of the present invention relates to the isolation of shikimic acid from a fermentation broth through a crystallization technique utilizing an organic acid, such as acetic acid.

BACKGROUND ART

U.S. Pat. No. 3,546,072 to Araki et al. discloses that 5-dehydroshikimic acid can be prepared by culturing a 5-dehydroshikimic acid producing microorganism of the genus Corynebacterium in a culture medium (fermentation broth), containing a carbon source, a nitrogen source, inorganic material and nutrients. The produced and accumulated 5-dehydroshikimic acid is isolated from the culture medium, after filtration to remove the microbial cells, through an adjustment of pH and the addition of active carbon. The active carbon absorbs the 5-dehydroshikimic acid and is eluded with 98% ethanol. The eluate is concentrated under reduced pressure and then the product precipitated from ethanol. This reference does not suggest or disclose the use of an organic acid such as acetic acid to enhance the precipitation of highly pure shikimic acid crystals from an aqueous fermentation broth.

U.S. Pat. No. 4,769,061 to Comai discloses a genetically modified plant wherein a gene encoding for a mutated glyphosate resistant 5-enolpyruvyl-3-phosphoskimimate synthase enzyme is included in the genome of the plant. This reference makes no suggestion of how to isolate shikimic acid from the tissue of such a genetically modified plant.

U.S. Pat. No. 5,214,165 to Sutherland et al. relates to 6-fluoroshikimic acid derivatives that have antibacterial, antifungal and herbicidal activity. This reference does not suggest the use of genetically modified microorganisms nor the use of glyphosate addition to a fermentation process to increase the production of shikimic acid. This reference further fails to suggest the use of an organic acid to assist in the isolation of shikimic acid from a fermentation broth. This reference does, however, disclose a class of PCCAs that are useful in the process of this invention.

U.S. Pat. No. 5,605,818 to Katsumata et al. discloses a process for producing an aromatic amino acid, such as tryptophan, through the use of culturing in a medium a mutant strain of the genus Corynebacterium or Brevibacterium. These mutant strains are capable of producing the desired aromatic amino acid and also have a higher transketolase activity than that of the parent strain. The desired aromatic amino acid is accumulated in the culture and recovered therefrom. This reference makes no suggestion of the use of an organic acid to isolate the desired PCCA from the broth. This reference does disclose a number of microorganisms that may produce a fermentation broth that is useful in the present invention.

An article entitled "Recovery of Shikimic Acid Using Temperature-Swing Complexation Extraction and Displacement Back Extraction" by Miles et al. in *Isolation & Purification*, 1994, Vol. 2, pp. 75–82, discloses a process for the removal of shikimic acid from aqueous solutions. The Miles et al. process is accomplished through solvent extraction using tridodecylamine dissolved in n-heptanol or n-butanol and back extraction to water using oleic acid to displace the shikimic acid from the organic phase. This reference focuses on developing a general method for recovering metabolic acids from fermentation broths. It fails, however, to disclose the use of acetic acid, which is added to a concentrated fermentation broth, to enhance the precipitation of shikimic acid from the broth.

An article from *Synthesis* of February, 1993 entitled: "The Biosynthesis and Synthesis of Shikimic Acid, Chorismic Acid and Related Compounds", pp. 179–193 by Campbell et al. teaches that compounds other than glyphosate may interfere with the shikimic acid pathway. This article also provides a good description of the glucose derived shikimate pathway and the various arduous approaches to the chemical synthesis of shikimic acid. This article makes no suggestion regarding the isolation of highly pure PCCA from reaction mixtures through the use of concentrated acetic, lactic and/or propionic acids.

In a publication by Jiang, et al. in *Tetrahedron* Report Number 449, Vol. 54 (1998), pp. 4697–4753, entitled:

"Chemical Synthesis of Shikimic Acid and Its Analogues" details are disclosed of the complex and arduous task of the synthesis of shikimic acid and its analogues. Jiang, et al., like Campbell, et al, fails to disclose the present invention.

SUMMARY OF THE INVENTION

There is disclosed a method for producing high purity (greater than 92% by wt.) crystals of polyhydroxy cyclic carboxylic acids (PCCA) from an aqueous solution which comprises:

a) concentrating the aqueous solution to a concentration of at least 250 gms of PCCA per liter; and b) combining said concentrated PCCA with at least one acid selected from the group consisting of acetic acid, lactic acid, propionic acid and mixtures thereof; and c) isolation of said crystal from said slurry.

There is also disclosed a method for producing high purity crystals of polyhydroxy cyclic carboxylic acids (PCCA) from aqueous solutions thereof comprising the steps of:

a) obtaining a solution of PCCA from any living organism capable of producing PCCA from aromatic amino acids, such as a microorganism (such as recombinant $E. coli$) or a plant. For example, the fermentation broth of a microorganism may be used to form a solution of PCCA;

b) concentrating the solution to a concentration of at least 450 gms of PCCA per liter;

c) combining the concentrated solution with at least one acid selected from the group consisting of acetic acid, lactic acid, propionic acid and mixtures thereof at a temperature of from 25 to 90° C. to form a PCCA/acid slurry;

d) cooling the PCCA/acid slurry to a temperature of from 25 to 5° C. to form crystals of the PCCA; and e) isolating the crystals from the slurry.

The PCCAs of the present invention comprise shikimic acid, quinic acid, 6-fluoroshikimic acid, dehydroshikimic acid and derivatives thereof and is, more preferably, shikimic acid.

There is further disclosed a method for producing high purity crystals of shikimic acid, the method comprising the steps of:

a) culturing a microorganism capable of producing aromatic amino acids in a medium by employing means to enhance the excretion of shikimic acid into the medium;

b) separating the microorganism from the medium to obtain an aqueous solution of shikimic acid;

c) concentrating the solution to a concentration of at least 450 gms of shikimic acid per liter to obtain a concentrated solution;

d) combining the concentration solution with concentrated acetic acid at a temperature in excess of 25° C. to obtain a shikimic acid/acid slurry;

e) cooling the shikimic acid/acid slurry to a temperature below 25° C. to obtain crystals of shikimic acid; and f) isolating the shikimic acid crystals from the slurry.

In general, the concentrated PCCA aqueous solution is combined with at least one acid selected from the group consisting of acetic acid, lactic acid, propionic acid and mixtures thereof to form a PCCA/acid slurry. This slurry is then cooled to a temperature of less than 25° C., preferably less than 10° C., most preferably to about 5° C., to form high purity crystals. The crystals are then isolated from the slurry using known techniques such as filtration and centrifugation.

There is further disclosed a method wherein the concentration of PCCA is at least 450 grams per liter and which additionally comprises the step of heating and agitating the PCCA/acid slurry to a temperature of from 25 to 90° C. prior to the cooling step. The cooling step is preferably accomplished in 1 to 8 hours.

In yet a more preferred embodiment, the concentration of the aqueous solution is at least 500 gms per liter, most preferably at least 600 gms per liter PCCA.

DETAILED DESCRIPTION OF THE INVENTION

In one embodiment, the present invention relates to a novel method of isolating high purity PCCAs from a fermentation broth through the addition of concentrated acetic, lactic and/or propionic acid to the broth. Acetic acid and glacial acetic acid ($CH_3COOH$) are colorless liquids with a pungent, irritating odor with a melting point of 16.6° C. and a boiling point of 118.8° C. They are miscible with water, alcohol and ether in all proportions. Acetic acid in diluted aqueous solutions is referred to as vinegar when fermentation processes are used to prepare it.

The lactic acids ($CH_3CHOHCOOH$) can be optically active and are colorless syrupy liquids which readily absorb moisture. These acids are formed by the fermentation of sugars by Lactobacilli and some molds. They are very soluble in water, but sparingly soluble in ether. The major use of the lactic acids is in the food and beverage industries, where it is used as an acidulate and for the manufacture of bread additives. It is also used as a chemical intermediate in textile finishing and in leather tanning.

Propionic acid ($CH_3CH_2COOH$) is a colorless liquid with an odor resembling that of acetic acid. It has a melting point of 24° C. and a boiling point of 140.7° C. It is miscible with water and alcohol.

The present invention can be applied to any PCCA, such as shikimic acid (mol. wt. 174, $C_7H_{10}O_5$), quinic acid (mol. wt. 192, $C_7H_{12}O_6$), dehydroshikimic acid (mol. wt. 172, $C_7H_8O_5$) and derivatives thereof. The most preferred PCCA is shikimic acid.

The PCCA may be prepared synthetically, isolated from plant material or produced through the use of native or genetically altered microorganisms (aerobic fermentation), such as $E. coli$. In any event, PCCAs present some difficulty in purification due to their high water solubilities. Typically, aqueous solutions of shikimic acid must be highly concentrated before crystallization can occur and this usually leads to a paste of crystals that are difficult to wash. While the use of organic solvents to purify these compounds to high levels (i.e., purities of greater than 92% by wt.) is possible, it would be advantageous to possess an aqueous based purification technique to avoid the numerous and known problems associated with organic solvents. It would also be advantageous to possess a process that is uncomplicated, economical, environmentally sound and accomplished without the use of complicated and expensive equipment. The present invention accomplishes all of these goals.

Shikimic acid produced by fermentation is especially problematic as the resulting fermentation broth contains a number of impurities that must be removed before the desired shikimic acid can be used as a nutritional supplement or as a starting material for the manufacture of pharmaceuticals. It would thus be an advancement in the state of the art if highly pure crystals of shikimic acid could be obtained for the relatively crude fermentation broth.

As mentioned previously, the source of the PCCA useful in the present invention may be obtained from any plant tissue, chemical synthesis, microorganisms or the like that produces shikimic acid in sufficient quantity to be economical. The method of the present invention becomes important when the need arises for high purity PCCAs to be isolated from rather crude raw materials, i.e., plant extracts, fermentation broths and the like. A preferred raw material for the method of the present invention is fermentation broth, more preferred are broths obtained form the conversion of glucose by microorganisms to shikimic acid, more particularly, the broths from fermentations that use glyphosate to control both the growth of the microorganism and to inhibit the enzymes like 5-enolpyruvyl-3-phosphoshikimate synthetase (EPSP synthetase)

While a means for enhancing the excretion of PCCAs into the culture medium through the inhibition of the enzymes is preferred, it is not necessarily solely achieved by addition of an enzyme inhibitor to one or more of the enzymes selected from shikimatekinase, EPSP synthetase and Chorismate synthase. The partial inhibition can also be achieved by genetic engineering of the genes encoding for shikimatekinase, EPSP synthetase and Chorismate synthase. The activity of one or more of the above mentioned enzymes is decreased to achieve accumulation of shikimic acid in the fermentation broth.

Alternatively, the activity of these enzymes can be limited through the use of feeding inorganic phosphate at a limiting rate. Any inhibitor, like glyphosate, that reduces the activity of the shikimatekinase, EPSP synthetase and the Chorismate synthase without impacting upon other activity of the organism can also be employed.

Irrespective of whether or not a genetically modified microorganism is utilized in the fermentation the present invention is directed to the utilization of an organic acid, such as acetic acid, to a semi-purified fermentation broth to enhance the precipitation of shikimic acid crystals from the concentrated broth.

Even more preferred are the broths where limited nutrient additions results in the accumulation of high levels of shikimic acid in the fermentation broth.

The genetic alteration of microorganisms to produce a desired result has been an active area of scientific research for some years. Recently, investigators have reported on the manipulation of microorganisms to enhance the excretion of PCCAs from the cells and into the culture medium or broth. Some of these genetic manipulations are metabolic manipulations and have been directed to increasing the flow of carbon into the shikimic pathway and stopping one of the reactions converting shikimic acid to Chorismate.

Yet another source of shikimic acid upon which the present invention can be conducted is obtained from fermentations wherein the carbon flow is increased into the shikimate pathway by combining metabolic manipulations during the fermentation. Further enhancement of the production of shikimic acid can be achieved through nutrient limitation. For example, the growth of microorganisms can be limited by limiting the cells' availability of aromatic amino acids (no exogenous source of aromatic amino acids exist in the growth medium). Alternatively, or in combination with the other techniques, shikimic acid production can be enhanced by feeding inorganic phosphate to the microorganisms at a growth limiting rate.

Any inhibitor can be used to restrict any of the enzymes that move shikimate through the metabolic pathway, provided it does not have any negative effect on the fermentation or the cells. In general, the addition of any enzymatic inhibitor, should not be so high as to kill the microorganism by depletion of the aromatic amino acids tryptophan, tyrosine, phenylalanine or the other metabolites diverging from chorismate, but should be high and often enough that increased accumulation of shikimic acid is achieved in the fermentation broth. Those skilled in the art will appreciate what parameters of cell growth, oxygen deletion and the like will have to be monitored to achieve the desired result.

In the process according to the invention, the fermentation broth is filtered to remove the cellular mass after the fermentation is complete. The cells are washed and the permeate is then passed over an anion exchange resin, for example AMBERLITE IRA458 Cl, manufactured by Rohmn and Haas, Paris Cedex 12, France. The column is eluted with an acid such as acetic acid. The eluate is then passed over a cation exchange resin, for example AMBERLITE IR120 Na, manufactured by Rohmn and Haas, Paris Cedex 12, France, where the impurities are retained. The solution is thereafter concentrated through the evaporation of water. The concentration of shikimic acid in the concentrate is about 250 to about 750 gms per liter, more preferably from 500 to 700 gms per liter and most preferably from 600 to 700 gms per liter. This concentrate then has added to it a crystallization acid selected from acetic acid, lactic acid, propionic acid and mixtures thereof. The crystallization acid is preferably added to the concentrate in pure form (i.e., concentrates such as glacial acetic acid), however, other high concentrations above 50% by wt. may be employed, at a temperature of from 30 to 90° C., more preferably 50 to 80° C. and most preferably from 65 to 75° C. The volume of crystallization acid added to the stirred concentrate can range from 0.5 to 2.0 times the volume of the concentrate, with 0.8 to 1.5 being most preferred and about 1.1 to about 1.4 being most preferred.

The mixture is then allowed to cool, preferably it is chilled to a temperature less than 25° C., more preferably less than 20° C. and most preferably less than 15° C. over a period of hours. The cooling step may take from 1 to 8 hours with 2 to 6 hours being more preferred. It is advantageous to have a controlled cooling of the slurry at about 10–20° C. per hour, more preferably about 15° C. per hour. After cooling, the mixture is now a slurry containing crystals of the desired PCCA. The crystals may be isolated by centrifugation or filtration using known procedures and apparatus. The crystals are then preferably washed with cooled and concentrated crystallization acid or acids. The crystals produced using this technique are of surprising purity, greater than 98% by wt. and yields of about 80% or more, are typical. This is quite surprising in light of the fact that the starting feed solutions are highly impure.

The following examples are provided for illustration and should not be construed as limiting the scope of the claims.

EXAMPLE I

A sample of shikimic acid was obtained from a commercial source and dissolved in water to a concentration of about 150 grams of shikimic acid per liter. This feed solution was evaporated to supersaturation in a Rotavac over a period of 1.5 to 2 hours at 70 to 80° C. to a concentration of 450 gms per liter. 100 ml of the supersaturated solution was placed in a glass beaker with a stir bar and 100 ml of glacial acetic acid was then added. The slurry was stirred at room temperature for about 16 hours and then placed in a refrigerator at 6° C., without stirring. After about 4 hours, 0.1 gm of shikimic acid crystals were added to the slurry to begin crystallization. The slurry remained at 6° C. for a total of 96 hours, however, a much shorter period of time would work just as well.

The crystals were separated from the solution through the use of a Buchner filter (paper filter Munktell No. 3). The crystals were then washed twice with 20 ml of an ethanol/ethyl acetate solution (1:1 vol.). The crystals were then dried at 40 to 50° C. for less than 1 hour. Ambient temperature drying could also be accomplished in about 3 to 5 hours.

EXAMPLE II

An aqueous solution of shikimic acid from the fermentation of *E. coli* (75% shikimic acid by wt. of total solids) was concentrated in a crystallizer to a concentration of 600 to 650 gms per liter. Concentrated warm acetic acid was added to the concentrate at 70° C. with stirring. During the addition of the acetic acid, the slurry was kept at about 70° C. The volume of acetic acid added was 1.1 times the volume of the concentrate. The slurry was cooled to 15° C. over a period of about 4 hours.

The crystals were then removed by centrifugation and washed with concentrated acetic acid until the filtrate was only slightly colored. Upon analysis, the crystals were 99% by weight shikimic acid and the yield was about 80% of theoretical.

EXAMPLE III

In a four-neck flask fitted with a stirrer and a thermometer was placed 190 ml of an aqueous solution of shikimic acid with a density of 1.0 gms per ml. The flask was in a bath at a temperature of 80 to 85° C. Under reduced pressure, water was distilled away until about 70 ml remained in the flask. The solution was brown in color. 100 ml of 100% acetic acid was then added and after about 30 minutes, crystals began to fall out of the solution. The slurry stood overnight (19 hours) at 20 to 25° C. with stirring. The slurry was then cooled to 6 to 8° C. over a period of about 5 hours with stirring. The crystals were removed by filtration and air-dried. The yellow crystals were then placed in a 350 ml flask and added thereto was 75 ml of ethyl acetate and 75 ml of ethanol. The slurry was allowed to stand for 30 minutes at 20 to 25° C. The crystals were then separated by filtration and washed with a mixture of 25 ml ethyl acetate and ethanol. The product was dried at 60° C. under reduced pressure.

EXAMPLE IV

The procedure described in Example III was used except that time, temperatures and amounts of the various components were altered. Table 1 sets forth the data for Examples IV through VIII.

EXAMPLE IX

Comparative 2.25 gms (0.0129 mol.) of shikimic acid, in solid form, (NMR purity of greater than 90% by wt.) was placed in flask and 15 ml of concentrate acetic acid was added thereto. The mixture was heated to boiling, resulting in a brown colored solution. The solution was then allowed to cool to 20° C. and stand for about 2 hours. A fine particulate precipitated and was filtered and washed with concentrated acetic acid and absolute ethanol. The crystals were dried and then analyzed for purity with an NMR. A yield of 1.20 gms was obtained (53% yield) and the purity was determined to be about 98% by wt.

EXAMPLE X

Comparative 0.96 gms of shikimic acid in solid form (NMR purity of greater than 90% by wt.) was heated to reflux in 30 ml of a 1 to 1 volume mixture of acetic acid and ethyl acetate. A minor quantity of undissolved material remained at the bottom of the flask, however, it dissolved upon the addition of about 3 ml of additional acetic acid. The solution was allowed to cool to room temperature and after 3 days, the crystals were filtered from the slurry, washed with ethyl acetate and dried. A yield of 0.52 gms was (54%) and the NMR purity was greater than 98% by weight. Cooling of the mother liquid to about 5° C. after filtering off the crystals, resulted in further precipitation of crystals. This was very slow and only an insignificant amount of crystals could be recovered.

EXAMPLE XI

Comparative

Example X was duplicated except the acetic acid/ethyl acetate mixture was replaced by an ethyl acetate/methanol mixture or absolute ethanol. The results were surprising in that only a very small amount of sparingly filterable crystals were obtained.

Industrial Applicability

Polyhydroxy cyclic carboxylic acids, such as shikimic acid, are important new metabolic nutritionals and starting materials for antiviral, antibacterial and other therapeutic agents. While shikimic acid can be synthesized using various chemical routes, it is costly and presents difficulty in obtaining the proper stereoisomer. These compounds can also be extracted from plant material, but clean up and

TABLE 1

| | Amt. of shikimic acid solution (ml) | Distillation vol. Remaining (ml) | Distillation Temp. | Mbar | Amt. of acetic acid (ml) | Mixing Time (Hr) | Temp (° C.) | Cooling Time (hr) | Temp (° C.) | Yield Gm | % of Theoretical |
|---|---|---|---|---|---|---|---|---|---|---|---|
| Ex. IV | 189 | 50 | 30.6° to 41.3° | 43 to 52 | 80 | 51 | 25° | 8.8 | 5.9° | 16.1 | 96.1 |
| Ex. V | 190 | n/a | 26° to 33.7° | 35 | 50 | 94 | 25° | n/a | n/a | 13.3 | 96.7 |
| Ex. VI | 189 | n/a | 28.8° to 44.2° | 39 to 45 | 100 | 1 | 25° | 8.8 | 6.2° | 28.3 | 98.4 |
| Ex. VII | 190 | 70 | 26.2° to 28.2° | 44 to 50 | 100 | 2 | 25° | 19 | 6.2° | 30.7 | n/a |
| Ex. VIII | 190 | 70 | 22.8° to 25.9° | 32 to 41 | 100 | 19 | 25° | 5 | 6° | 28.2 | n/a | n/a = not available obtaining the high level of purity required is also problematic from this source. The use of microorganisms to produce shikimic acid has been shown to be cost effective and practical, however, the isolation of high purity shikimic acid from the fermentation broth has also presented difficult hurdles to overcome. One aspect of the present invention provides an effective means to obtain high purity shikimic acid crystals from a crude aqueous solution of shikimic acid. The surprising results are obtained through the use of a special group of acids, more specifically, acetic, propionic and lactic acids in a crystallization process that does not use organic solvents or elaborate temperature-swing complexation extractions and displacement back extractions.

Although the foregoing invention has been described in some detail by way of illustration and examples, for purposes of clarity of understanding, it will be apparent to those skilled in the art that certain changes and modifications may be practiced within the scope of the appended claims.

What is claimed is:

1. A method for producing high purity crystals of polyhydroxy cyclic carboxylic acids (PCCA) from an aqueous solution thereof which comprises:
   a) concentration of an aqueous solution of said PCCA to a concentration of at least 250 grams of said PCCA per liter;
   b) combining said concentrated PCCA with at least one acid selected from the group consisting of acetic acid, lactic acid, propionic acid and mixtures thereof to form a PCCA/acid slurry; and
   c) isolation of said crystals from said slurry.

2. The method according to claim 1 wherein said PCCA is selected from shikimic acid, quinic acid, dehydroshikimic acids, 6-fluoroshikimic acid, and derivatives thereof.

3. The method according to claim 1 wherein said concentration of said PCCA is at least 450 grams per liter.

4. The method according to claim 1 wherein said acid is shikimic acid.

5. The method according to claim 1 which additionally comprises cooling said PCCA/acid slurry to a temperature less than 25° C. to form high purity crystals of said PCCA.

6. The method according to claim 5, which additionally comprises the step of heating and agitating the PCCA/acid slurry prior to the cooling step.

7. The method according to claim 6 wherein said heating step heats the PCCA/acid slurry to a temperature of from 25° to 90° C.

8. The method according to claim 5 wherein said cooling step is accomplished in 1 to 8 hours.

9. The method according to claim 8 wherein said slurry is cooled to a temperature of less than 10° C.

10. The method according to claim 1 wherein said acid is concentrated.

11. The method according to claim 1 wherein said aqueous solution of PCCA is obtained from the fermentation of microorganisms.

12. A method for producing high purity crystals of polyhydroxy cyclic carboxylic acids (PCCA) from aqueous solutions thereof comprising the steps of:
   a) obtaining a solution of PCCA from the fermentation broth of an organism,
   b) concentrating said solution to a concentration of at least 450 gms of PCCA per liter;
   c) combining said concentrated solution with at least one acid selected from the group consisting of acetic acid, lactic acid, propionic acid and mixtures thereof at a temperature of from 25 to 90° C. to form a PCCA/acid slurry;
   d) cooling said PCCA/acid slurry to a temperature of from 25 to 5° C. to form crystals of said PCCA; and
   e) isolating said crystals from said slurry.

13. The method according to claim 12 wherein said PCCA is shikimic acid; said organism is *E. coli*; said concentration of said solution is at least 500 gm per liter; said acid is concentrated acetic acid; and wherein the volume of said concentrated solution can range from 0.5 to 2.0

14. The method according to claim 13 wherein said *E. coli* is a genetically modified organism; the concentration of said solution is at least 600 gms per liter of PCCA; and wherein the volume of said concentrated acetic acid to the volume of said concentrated solution can range from 1.1 to about 1.4.

15. A method for producing high purity crystals of shikimic acid, said method comprising the steps of:
   a) culturing in a medium an organism capable of excretion shikimic acid into said medium;
   b) separating said microorganism from said medium to obtain an aqueous solution of shikimic acid;
   c) concentrating said solution to a concentration of at least 450 gms of shikimic acid per liter to obtain a concentrated solution;
   d) combining said concentrated solution with concentrated acetic acid at a temperature in excess of 25° C. to obtain a shikimic acid/acid slurry;
   e) cooling said shikimic acid/acid slurry to a temperature below 25° C. to obtain crystals of shikimic acid; and
   f) isolating said shikimic acid crystals from said slurry.

16. The method according to claim 15 wherein said means to enhance excretion of shikimic acid is selected from; genetic engineering of the genes encoding for shikimatekinase, EPSP synthetase and Chorismate synthase; and adding inorganic phosphate at a limiting rate to the medium.

* * * * *